PROCESS FOR THE PREPARATION OF 2-ALKOXYTETRAHYDROFURANS VIA HYDROFORMYLATION OF ALLYLIC ALCOHOLS

The present invention relates to an improved preparation of 2-alkoxytetrahydrofurans and their derivatives. More particularly it relates to an improved process for the hydroformylation of allylic alcohols in the presence of a rhodium catalyst and an alkanol solvent/co-reactant, in which an acid co-catalyst is employed.

BACKGROUND OF THE INVENTION

2-Alkoxytetrahydrofurans and their derivatives are useful intermediates in the production of 1,4-diols and other valuable chemicals. See the co-pending application of William Edward Smith, Ser. No. 806,074, filed June 13, 1977.

A new process for the production of 2-alkoxytetrahydrofurans and their derivatives by an oxo tetrahydrofuranylation reaction comprising the hydroformylation of allylic alcohols in the presence of saturated alcohols and rhodium carbonyl catalysts is described in applicant's co-pending application Ser. No. 806,703, filed June 13, 1977, and incorporated herein by reference. The process was discovered when a triphenylarsine-modified rhodium carbonyl catalyst was used in the conventional hydroformylation of allyl alcohol — some 2-n-propoxytetrahydrofuran was found among the reaction products. As is described in the latter application, when solvent or coreactant quantities of methanol, n-propanol, etc., are present, good to excellent yields of the corresponding alkoxytetrahydrofurans are produced depending on the allylic alcohol substrate.

The role of the triphenylarsine catalyst component in the initial work appears to have been more than incidental. Triphenylarsine appears to form a relatively weak complex with the rhodium carbonyl hydride catalyst intermediate, e.g., $$H\ Rh(CO)_3L$$

wherein L is $As(C_6H_5)_3$. This complex is apparently quite acidic, rather than hydridic, as is indicated by the ready formation of 1,1-dimethoxypropane from methanol and propionaldehyde in a side reaction.

In contrast, the triphenylphosphine/rhodium carbonyl catalyst system, also described in the second-mentioned application, does not seem to exhibit the same "acidic" character. While triarylphosphine complexed catalysts are excellent hydroformylation catalysts, they do have the disadvantage of not favoring the conversion of the intermediate 2-hydroxy-tetrahydrofuran or substituted-tetrahydrofuran to the corresponding 2-alkoxytetrahydrofurans without extended and/or vigorous heating.

It has been discovered that the new oxo tetrahydrofuranylation process can be improved by the use of acids as co-catalysts for the rhodium carbonyl/tertiaryphosphine complex catalyst. The new rhodium carbonyl/tertiaryphosphine/acid co-catalyst system is superior to rhodium carbonyl/tertiaryphosphine with respect to the yield of the more stable 2-alkoxy product, a finding which has important implications relative to production of 1,4-butanediol from allyl alcohol via 2-methoxytetrahydrofuran or other 2-alkoxytetrahydrofurans.

Merely by way of illustration, o-phthalic acid serves the co-catalytic function well without promoting undesired side reactions. It is strong enough as an acid to promote the conversion of the intermediate 2-hydroxytetrahydrofuran to the 2-alkoxy product, but does not significantly decompose the other initial oxo product, 3-hydroxy-2-methylpropionaldehyde. Moveover, the fact that the acid co-catalyst does not interfere with the hydroformylation reaction itself is entirely unexpected. The hydrolysis-hydrogenation step according to the present discovery produces the potentially valuable 2-methyl-1,3-propanediol as the major byproduct (about 30:70 vs. 1,4-butanediol), with only minor amounts of n-propanol and isobutanol formed. Such transformations are illustrated in the following pathway:

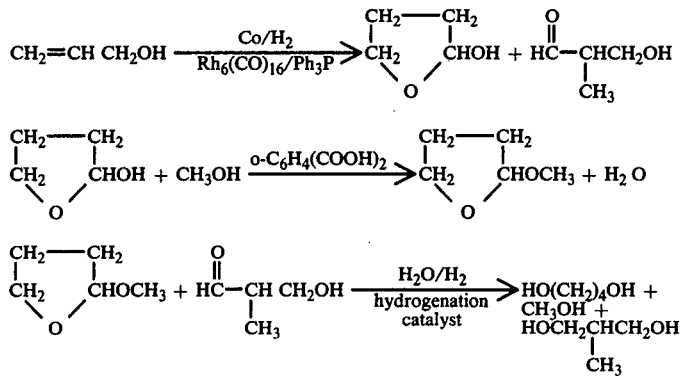

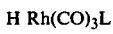

In a controlled comparison of the hydroformylation of allyl alcohol in the presence of methanol with a rhodium carbonyl/triphenylphosphine catalyst per se, and also complexed with o-phthalic acid co-catalyst according to this invention, the ratio of 2-methoxytetrahydrofuran to 2-hydroxytetrahydrofuran at 115° C. was markedly and favorably altered by the co-catalyst from 6:94, without, to 97.3, with.

DESCRIPTION OF THE INVENTION

According to the present invention in its broadest aspects there is provided an improved process for preparing a 2-alkoxytetrahydrofuran or a 2-alkoxy-substituted tetrahydrofuran in which an allylic alcohol, carbon monoxide, hydrogen and the corresponding alkanol are contacted with a rhodium triarylphosphine hydroformylation catalyst in combination with an acid co-catalyst.

[54] PROCESS FOR THE PREPARATION OF 2-ALKOXYTETRAHYDROFURANS VIA HYDROFORMYLATION OF ALLYLIC ALCOHOLS

[75] Inventor: William E. Smith, Schenectady, N.Y.

[73] Assignee: General Electric Company, Pittsfield, Mass.

[21] Appl. No.: 849,435

[22] Filed: Nov. 7, 1977

[51] Int. Cl.$^2$ ............................................. C07D 307/20
[52] U.S. Cl. .................................................... 260/347.8
[58] Field of Search ....................................... 260/347.8

[56] References Cited

U.S. PATENT DOCUMENTS

| | | | |
|---|---|---|---|
| 3,239,566 | 3/1966 | Slaugh et al. | 260/604 |
| 3,917,661 | 11/1975 | Pruett et al. | 260/410.9 R |

FOREIGN PATENT DOCUMENTS

| | | |
|---|---|---|
| 103203 | 3/1962 | Czechoslovakia. |
| 2538364 | 3/1976 | Fed. Rep. of Germany. |

OTHER PUBLICATIONS

Adkins et al., Journal of the American Chemical Society, vol. 70 (1948), pp. 383–386 and vol. 71 (1949) pp. 3051–3055.
Lawesson et al., Acta. Chem. Scand., vol. 14 (1960) pp. 1854–1855.
Brown et al., Tetrahedron Letters, vol. 22 (1969), pp. 1725–1726.
Brown et al., Journal of the Chemical Society (A), 1970, pp. 2753–2764.

*Primary Examiner*—Richard Raymond
*Attorney, Agent, or Firm*—Morgan, Finnegan, Pine, Foley & Lee

[57] ABSTRACT

2-Alkoxytetrahydrofurans are prepared in higher yields when an allylic alcohol is hydroformylated in the presence of an alkanol and a rhodium/tertiaryphosphine-complex if an acid co-catalyst is used. The products are useful, inter alia, as intermediates in the preparation of butanediols and substituted derivatives thereof.

13 Claims, No Drawings

The process may be carried out batchwise or on a continuous or semicontinuous basis. Typically in a continuous or semicontinuous process, the allylic alcohol and alkanol are supplied to a reactor in which the temperature and pressure conditions for reaction are already established. The reactor will also contain the solvent and the catalyst. The products can be isolated by distillation, and the catalyst can be recycled to the reactor in the distillation residue.

Such techniques are well known to those of ordinary skill in the art.

DESCRIPTION OF THE PREFERRED EMBODIMENTS

The following examples are set forth to illustrate the present invention. They are not to be construed to limit the claims in any manner whatsoever.

Comparative Procedure A (a) 2-Methoxytetrahydrofuran by Hydroformylation in the Absence of Acid Co-Catalyst A 300 cc. Autoclave Engineers Magnedrive Autoclave is charged with 50.0 g. of allyl alcohol (861 mmol.), 75.0 g. of methanol (2.34 mol). 0.202 g. of hexarhodium hexadecacarbonyl (0.189 mmol., 1.14 meq. Rh), and 9.6 of triphenylphosphine (36.6 mmol.). The mixture is subjected to 1200 psi. of 1:1 H/CO and heated at 115° C. for 20 minutes from onset of gas uptake, then cooled (4000 psi total uptake, replenished at 800–1200 psi). Analysis of the product mixture by gas liquid partition chromatography (glpc) shows the presence of 2-hydroxytetrahydrofuran and 2-methoxytetrahydrofuran in 94:6 ratio, in addition to 3-hydroxy-2-methylpionaldehyde and several other high boiling compounds. The mixture is chilled and decanted from the substantial portion of triphenylphosphine that crystallizes.

(b) 1,4-Butanediol

The bulk (89%) of product solution from step (a) is combined in the autoclave with 50 ml. of water and 10.0 g. of 50% nickel on kieselguhr catalyst. This mixture is heated at 75° C. under 800–1000 psi of hydrogen for 2 hours (3100 psi gas uptake) then cooled and filtered. Rotary evaporation of the filtrate leaves 59.2 g. of mixed diols (66.3 g. corrected), contaminated with a small amount of triphenylphosphine. Quantitative glpc analysis shows presence of 41.4 g. of 1,4-butanediol (corrected, 60% yield based on allyl alcohol), and 17.8 g. of 2-methyl-1,3-propanediol (19.9 g. corrected, 26% yield).

EXAMPLE I (a) 2-Methoxytetrahydrofuran by Hydroformylation in the Presence of Phthalic Acid Co-Catalyst The exact procedure as described for A is followed, but with the addition of 1.43 g. of o-phthalic acid (8.61 mmol.). In this case 4550 psi of gas is taken up. Analysis of the product mixture shows presence of the 2-hydroxy-tetrahydrofuran and 2-methoxytetrahydrofuran in 3:97 ratio, along with the 3-hydroxy-2-propionaldehyde and other high boiling compounds. The yield of 2-methoxytetrahydrofuran is about 53 g. (60%), estimated by quantitative glpc analysis and by $^1$H nmr analysis of the mixture.

(b) 1,4-butanediol

A major portion (57%) of the product mixture of step (a) is combined with 50 ml. of water and 10.0 g. of the nickel catalyst described in Procedure A. The hydrogenation (hydrolysis) reaction in this case is considerably slower. In four hours at 75° C./800–1000 psi, about 80% of the 2-methoxytetrahydrofuran initially present is converted (1300 psi gas uptake). The hydrolysis-hydrogenation product is filtered and concentrated by rotary evaporation. The concentrate is extracted with pentane to remove the triphenylphosphine, then subjected to further rotary evaporation. The residue is composed almost exclusively of the two diols. Quantitative analysis shows the presence of 22.5 g. of 1,4-butanediol (39.6 g. corrected, 64% yield based on allyl alcohol and on the 80% conversion of the 2-methoxytetrahydrofuran intermediate), and 13.2 g. of 2-methyl-1,3-propinediol (23.2 g. corrected, 30% yield based on allyl alcohol.

The results are summarized in Table I.

TABLE I

Effect of Phthalic Acid Co-Catalyst on the Oxo Tetrahydrofuranylation of Allyl Alcohol

| Co-Catalyst | Diol Precursor Products | 2-Methoxy/2-Hydroxy Ratio | 1,4-butane-diol, % | 2-methyl-1,3-propane-diol, % |
|---|---|---|---|---|
| None[a] | 2-hydroxy-tetrahydrofuran 3-hydroxy-2-methylpropion-aldehyde 2-methoxy-tetrahydrofuran | 6:94 | 60 | 26 |
| o-phthalic acid[b] | 2-methoxy-tetrahydrofuran 3-hydroxy-2-methylpropion-aldehyde 2-hydroxy-tetrahydrofuran | 97:3 | 64 | 30 |

[a]Comparative procedure A: Reaction Time, 20 min., 115° C., 1:1 H$_2$/CO at 500–1200 psi; methanol: allyl alcohol: triphenyl phosphine: rhodium = 2053:755 : 32:1
[b]Example I, same as [a] with phthalic acid: rhodium = 7.5:1

The ability of phthalic acid to promote the process as a co-catalyst without promoting undesired side reactions and without interfering with the hydroformylation reaction itself is clearly shown.

EXAMPLE II

2-Isobutoxytetrahydrofuran

The autoclave is charged with 50.0 g. of allyl alcohol (861 mmol.), 111.7 g. of isobutanol (1.50 mol.). 0.202 g. of hexarhodium hexadecacarbonyl (0.189 mmol.. 1.14 meq. Rh), 9.6 of triphenylphosphine (36.6 mmol.) and 2.86 g. of phthalic acid (17.2 mmol.), then heated at 125° C. under replenished 800–1200 psi 1:1 H$_2$/CO for one hour. Quantitative glpc analysis of the product mixture shows the presence of 61.0 g. 2-isobutoxytetrahydrofuran (49% yield) identified based on ir, nmr. and mass spectra which are in complete accord with the assignment. Another product present in relatively minor amount is isolated and identified as 3-(α-tetrahydrofuranyloxy)-2-methyl-propionaldehyde on the basis of its i r spectrum.

EXAMPLE III

2-n-Propoxytetrahydrofuran

The procedure of Example I, step (a) is repeated, substituting a stoichiometrically-equivalent amount of n-propanol for methanol, and 2-n-propoxytetrahydrofuran is obtained.

EXAMPLE IV

2-Methoxytetrahydrofuran Using 4,5-Dichloro-o-Phthalic as Co-Catalyst

The procedure of Example I step (a) is repeated substituting a stoichiometrically-equivalent amount of 4,5-dichloro-o-phthalic acid for o-phthalic acid, and substantially the same results are obtained.

EXAMPLE V

The procedure of Example II is repeated, substituting 75.0 g. of methanol for the isobutanol and 2.0 g. of 86% phoshoric acid for the phthalic acid. Quantitative glpc ananlysis shows the presence of 47.0 g. of 2-methoxytetrahydrofuran (55% yield).

In other experiments, benzenesulfonic acid and toluenesulfonic acid both appeared ineffective as co-catalysts when used in low concentration, possibly because of reaction with the triphenylphosphine. Similarly, a strong acid ion exchange resin (Dowex WX16) was ineffective in the presence of triphenylphosphine in promoting the reaction of 2-hydroxy-5,5-dimethyltetrahydrofuran and allyl alcohol to produce 2-allyloxy-5,5-dimethyltetrahydrofuran. Phthalic acid did effectively catalyze this reaction.

Phthalic acid has a $pK_a$ of 2.89($K_1$), and a dissociation constant of $1.3 \times 10^{-3}$ in aqueous solution. This level of acid strength may be ideal for the co-catalysis function as described.

Obviously, minor variations will suggest themselves to those skilled in the art in view of the above-identified description. For example, if methallyl alcohol is used instead of allyl alcohol, the corresponding product, 2-methoxy-4-methyltetrahydrofuran will be produced. If 2-methyl-3-butane-2-ol is used, the corresponding product, 2-isobutoxy-5,5-dimethyltetrahydrofuran will be produced in about 85% yield. Moreover, heterogeneous acidic co-catalysts can also be used, e.g., alumina, silica, tungsten oxide, although they are not preferred. All such obvious modifications are within the full intended scope of the appended claims.

I claim:

1. In a process for preparing a 2-alkoxytetrahydrofuran or 2-alkoxy-substituted tetrahydrofuran by contacting an allylic alcohol, carbon monoxide, hydrogen and a corresponding alkanol with a rhodium/tertiaryphosphine complex hydroformylation catalyst, the improvement which comprises using an acid co-catalyst with such rhodium complex catalyst, said acid co-catalyst being both (i) strong enough to promote the desired conversion yet not so strong as to significantly decompose initial oxo products and (ii) inert with respect to the reactants.

2. A process as defined in claim 1 wherein said co-catalyst has a $pK_a$ of from about 1.5 to about 3.5 in aqueous solution.

3. A process as defined in claim 1 carried out at a pressure in the range of 100–5000 psi.

4. A process as defined in claim 3 carried out at a pressure in the range of 300–1200 psi.

5. A process as defined in claim 1 carried out at a temperature between about 25° C. and 200° C.

6. A process as defined in claim 5 carried out at a temperature in the range of 70–150° C.

7. A process as defined in claim 1 wherein said triarylphosphine is triphenylphosphine.

8. A process as defined in claim 1 wherein said allylic alcohol comprises allyl alcohol, methallyl alcohol or 2-methyl-3-buten-2-ol.

9. A process as defined in claim 1 wherein said alkanol comprises methanol, n-propanol or isobutanol.

10. A process as defined in claim 1 wherein said allylic alcohol is selected from those of the formula:

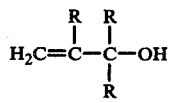

wherein R is hydrogen or alkyl from 1 to 8 carbon atoms and said alkanol is selected from among those of the formula:

wherein $R^1$ is alkyl of from 1 to 8 carbon atoms or hydroxyalkyl of from 2 to 8 carbon atoms.

11. In a process for preparing a 2-alkoxytetrahydrofuran or 2-alkoxy-substituted tetrahydrofuran by contacting an allylic alcohol, carbon monoxide, hydrogen and a corresponding alkanol with a rhodium/tertiaryphosphine complex hydroformylation catalyst, the improvement which comprises using an o-phthalic acid co-catalyst with such rhodium complex catalyst.

12. In a process for preparing a 2-alkoxytetrahydrofuran or 2-alkoxy-substituted tetrahydrofuran by contacting an allylic alcohol, carbon monoxide, hydrogen and a corresponding alkanol with a rhodium/tertiaryphosphine complex hydroformylation catalyst, the improvement which comprises using a 4,5-dichlorophthalic acid co-catalyst with such rhodium complex catalyst.

13. In a process for preparing a 2-alkoxytetrahydrofuran or 2-alkoxy-substituted tetrahydrofuran by contacting an allylic alcohol, carbon monoxide, hydrogen and a corresponding alkanol with a rhodium/tertiaryphosphine complex hydroformylation catalyst, the improvement which comprises using a phosphoric acid co-catalyst with such rhodium complex catalyst.

* * * * *

UNITED STATES PATENT AND TRADEMARK OFFICE
CERTIFICATE OF CORRECTION

PATENT NO. : 4,139,542

DATED : February 13, 1979

INVENTOR(S) : William F. Smith

It is certified that error appears in the above-identified patent and that said Letters Patent are hereby corrected as shown below:

Column 2, line 58, "97.3" should read -- 97:3 --.

Signed and Sealed this

Sixteenth Day of October 1979

[SEAL]

Attest:

RUTH C. MASON
Attesting Officer

LUTRELLE F. PARKER
Acting Commissioner of Patents and Trademarks